(12) United States Patent
Scheffel

(10) Patent No.: US 9,498,373 B2
(45) Date of Patent: Nov. 22, 2016

(54) ORAL DEVICE FOR IMPROVEMENT OF BREATHING

(71) Applicant: Bernd Scheffel, Munich (DE)

(72) Inventor: Bernd Scheffel, Munich (DE)

(73) Assignee: BERND SCHEFFEL, Munich (DE)

( * ) Notice: Subject to any disclaimer, the term of this patent is extended or adjusted under 35 U.S.C. 154(b) by 470 days.

(21) Appl. No.: 13/773,513

(22) Filed: Feb. 21, 2013

(65) Prior Publication Data

US 2013/0220341 A1  Aug. 29, 2013

(30) Foreign Application Priority Data

Feb. 23, 2012  (DE) .................... 10 2012 003 564

(51) Int. Cl.
| | |
|---|---|
| A61C 5/14 | (2006.01) |
| A61C 3/00 | (2006.01) |
| A61C 19/04 | (2006.01) |
| A61F 5/56 | (2006.01) |
| A61C 19/00 | (2006.01) |
| A61C 11/00 | (2006.01) |
| A61C 7/00 | (2006.01) |
| A61C 19/045 | (2006.01) |
| A61C 7/10 | (2006.01) |
| A61C 7/08 | (2006.01) |

(52) U.S. Cl.
CPC ................ *A61F 5/566* (2013.01); *A61C 7/00* (2013.01); *A61C 7/08* (2013.01); *A61C 7/10* (2013.01); *A61C 11/00* (2013.01); *A61C 19/00* (2013.01); *A61C 19/04* (2013.01); *A61C 19/045* (2013.01); *A61F 5/56* (2013.01); *Y10T 29/49826* (2015.01)

(58) Field of Classification Search
CPC .... A61F 5/56; A61F 2005/563; A61F 5/566; A61C 11/00; A61C 19/00; A61C 19/04; A61C 19/045

USPC ................ 128/848, 859, 861, 862; 433/5–7, 433/18–19, 22, 24, 68–69; 602/902
See application file for complete search history.

(56) References Cited

U.S. PATENT DOCUMENTS

| | | | |
|---|---|---|---|
| 6,450,167 B1 * | 9/2002 | David et al. .................. | 128/848 |
| 7,810,502 B1 * | 10/2010 | Nguyen et al. ............... | 128/848 |
| 7,987,854 B2 * | 8/2011 | Arni .............................. | 128/848 |
| 2007/0006884 A1 * | 1/2007 | Abramson .................... | 128/848 |
| 2010/0304321 A1 * | 12/2010 | Patel ............................. | 433/9 |
| 2011/0232651 A1 * | 9/2011 | Diers ........................... | 128/848 |
| 2011/0308531 A1 * | 12/2011 | Grosky ......................... | 128/848 |

FOREIGN PATENT DOCUMENTS

DE  102008007281  *  8/2009  ............... A61F 5/56

* cited by examiner

*Primary Examiner* — Alireza Nia
*Assistant Examiner* — Brandon L Jackson
(74) *Attorney, Agent, or Firm* — Robert Becker; Berenbaum Weinshienk PC

(57) ABSTRACT

An oral device for improving the breathing of a user by means of protrusion of the lower jaw includes a first dental rail that covers at least some teeth of a lower row of teeth of the user; a second dental rail that covers at least some teeth of an upper row of teeth of the user; and at least one coupling element connecting the first and the second dental rail. The first dental rail comprises a front, labial connection point and the second dental rail has two rear, buccal connection points positioned substantially at its two posterior ends. The coupling element has a substantially U-shaped configuration, and an apex of the coupling element forms a joint with the front labial connection point on the first dental rail. The posterior ends of the coupling element form a joint with the rear connection points of the second dental rail.

10 Claims, 6 Drawing Sheets

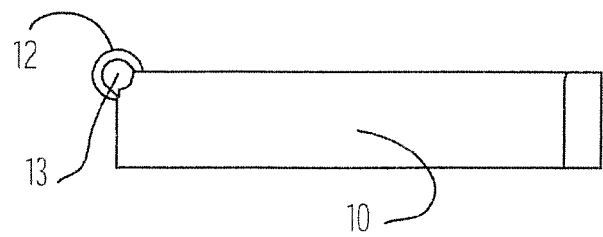
Fig. 4.1
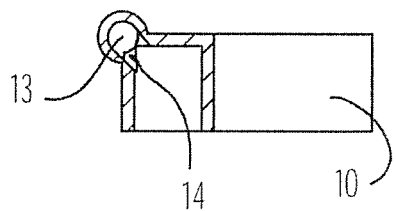
Fig. 4.2
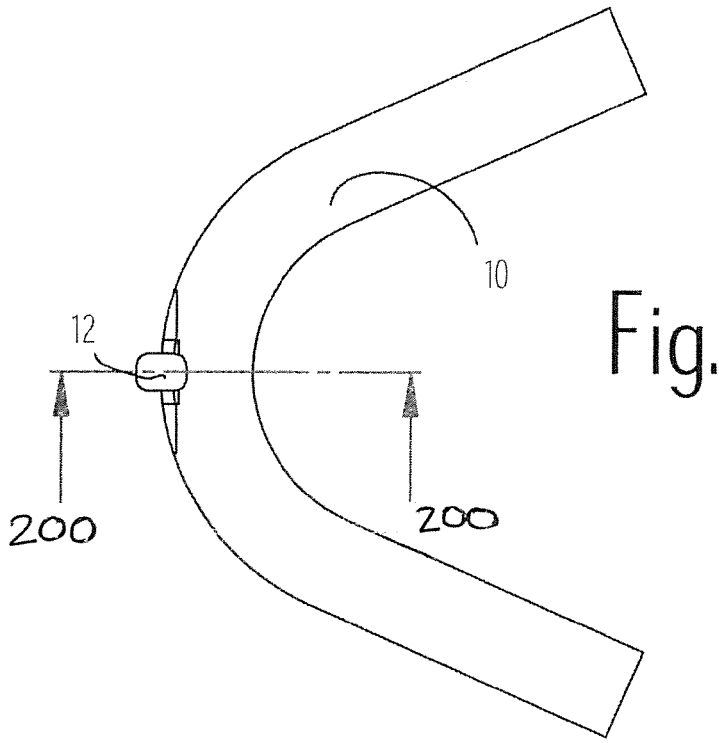
Fig. 4.3
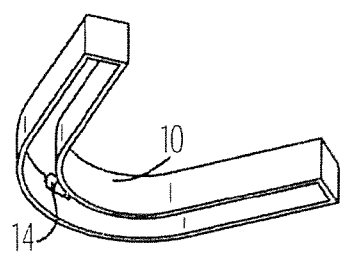
Fig. 4.4

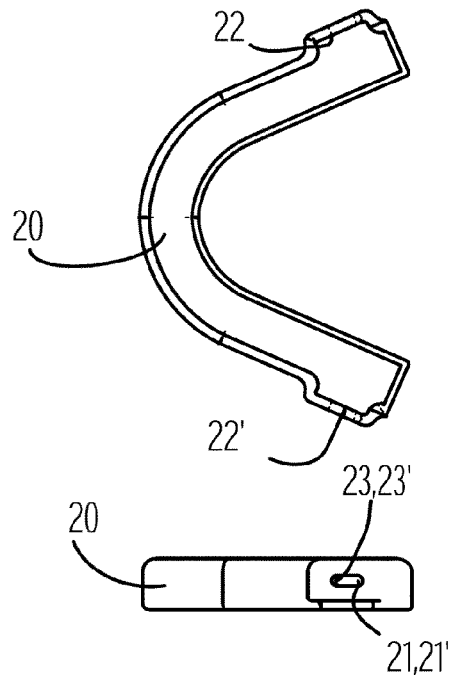
Fig. 5.1
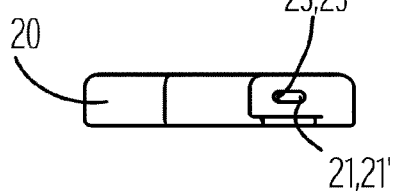
Fig. 5.2
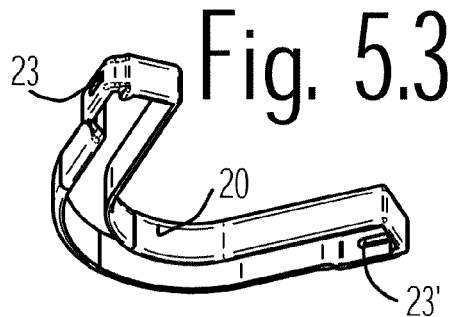
Fig. 5.3
Fig. 6.1
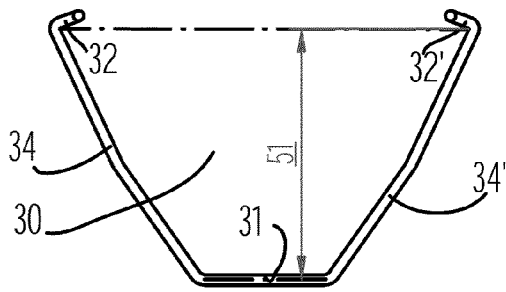
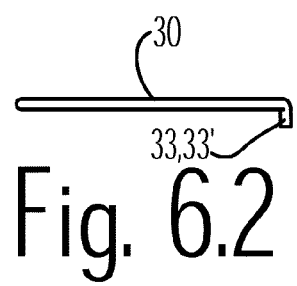
Fig. 6.2
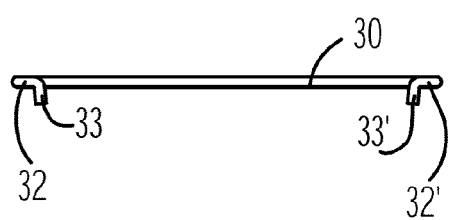
Fig. 6.3

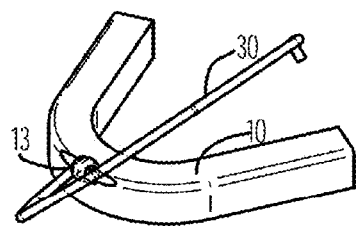
Fig. 7.1
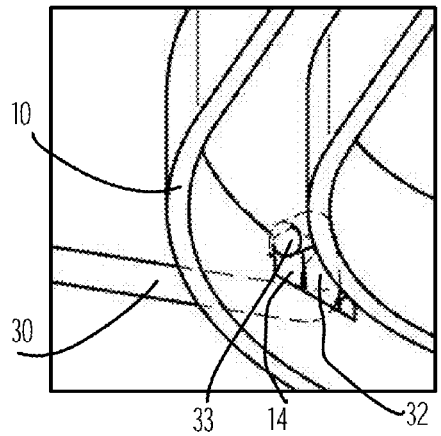
Fig. 7.2
Fig. 7.3
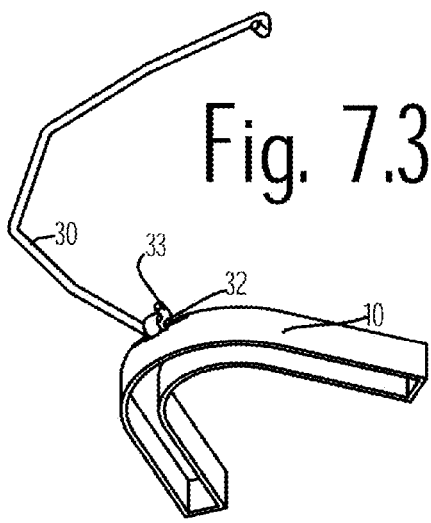
Fig. 7.4
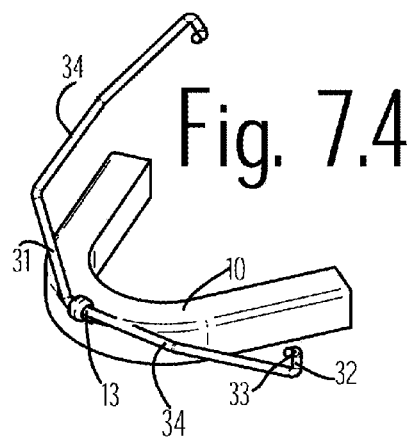
Fig. 7.5
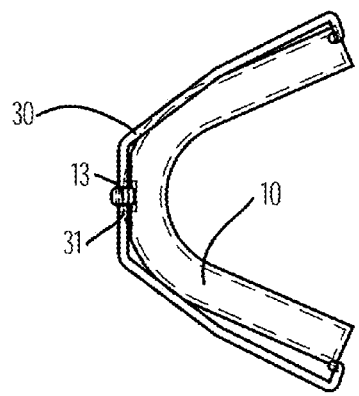

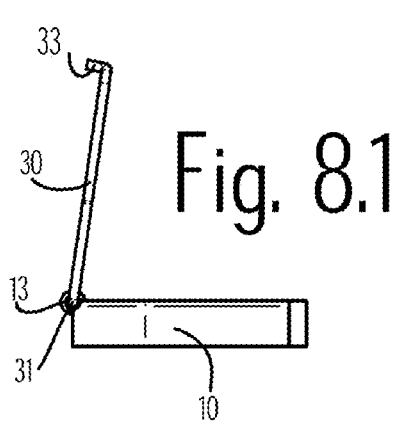
Fig. 8.1
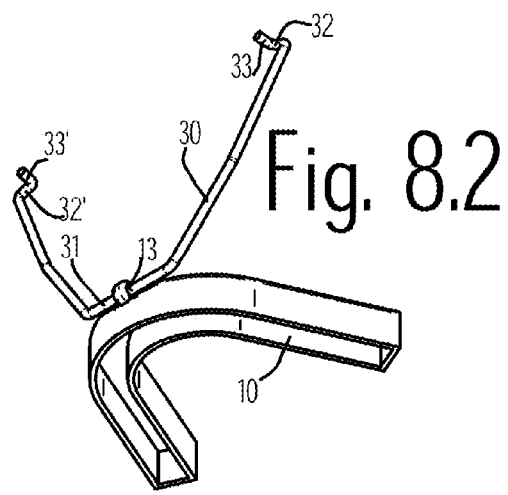
Fig. 8.2
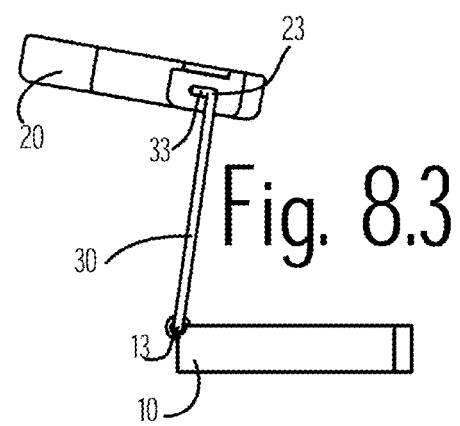
Fig. 8.3
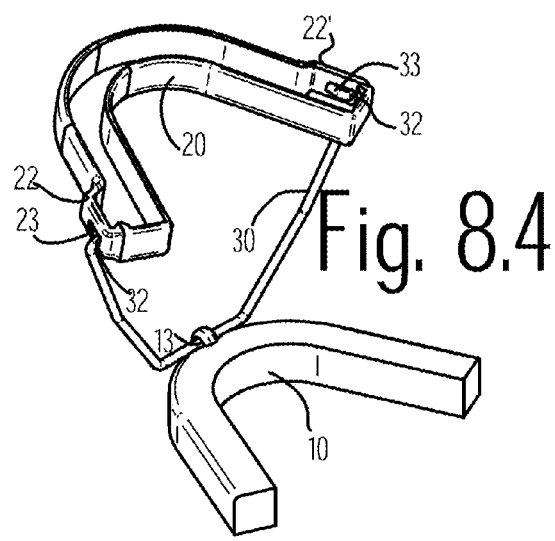
Fig. 8.4
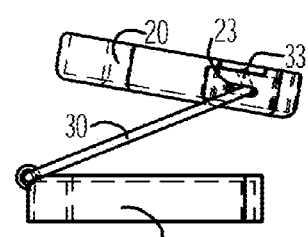
Fig. 8.5
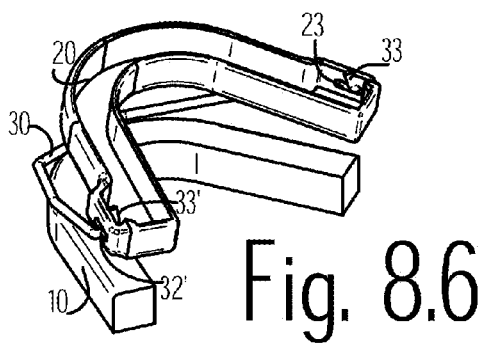
Fig. 8.6

Fig. 9.1
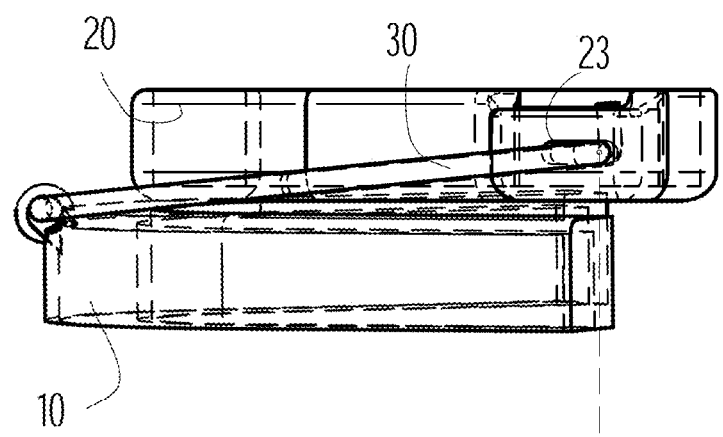
Fig. 9.2
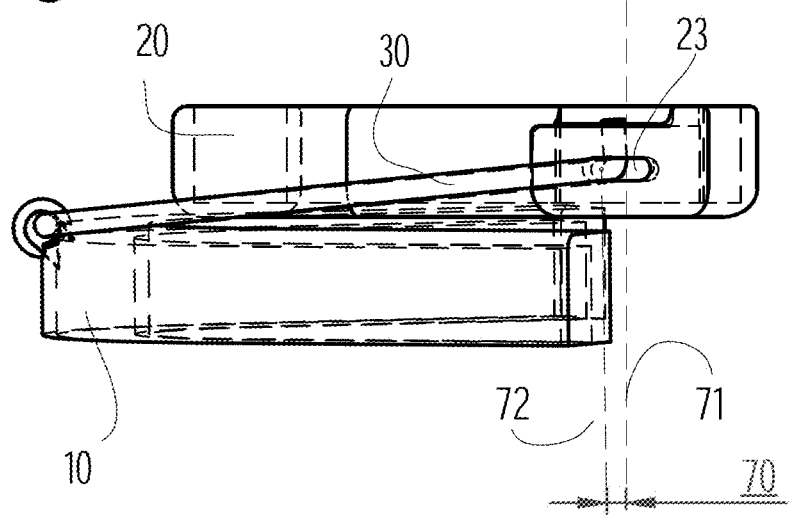

ORAL DEVICE FOR IMPROVEMENT OF BREATHING

BACKGROUND OF THE INVENTION

The present invention relates generally to oral devices and particularly to a device for improving the breathing of a user.

It is known that the mandibular advancement to help with obstructive breathing disorders has been used successfully. Applications are known for sleep apnea and snoring. Therapeutic successes have been achieved, especially with such devices with rails for the upper and lower dental arch which are custom made for the user.

Such systems require coupling elements between the two rails, which cause the mandibular advancement required by the therapy. Many embodiments of these coupling elements are possible.

Devices that are worn inside the dental arch influence the users comfort, disrupt the speech and the swallowing and can lead to increased salivation. Examples of such models with coupling elements inside the dental arch are described in DE20319088U1 and EP1312319A2.

Other devices with arrangement inside the dental arch and labial, are shown in DE 69501111T2, WO 2005013867A2, and U.S. Pat. No. 6,305,378B1 and allow only a small opening of the mouth. Where adjusting devices are proposed for the advancement, they cause additional deterioration of wearing comfort, as they occupy a portion of the tongue space. Because the tongue cannot reach the lips, the user cannot moisturize the lips with his tongue. Therefore, an important feature for the wearer's comfort is missing.

The arrangement of the coupling elements outside of the dental arch, as well as labially, allows little mouth opening, as shown in DE112009001742T5. Moreover, the mouth cannot be completely closed, which leads to undesired mouth breathing. Thus, speaking is impaired, as the tongue cannot reach the lips and the user cannot moisturize the lips with his tongue.

Coupling elements labially arranged outside of the dental arch need less space, as shown in DE 102008007281A1, as long as a complex adjusting device for the advancement is absent. A coupling element between the two rails is a curved guide member, whose ends are connected with both sides of the second rail. The opening of the mouth is limited. When trying to open the mouth further, forces result which remove the rails from the dental arches. That way the effect of the system is lost.

A frequently proposed arrangement of coupling elements uses two coupling elements and four joints buccally outside of the arch.

Tensile forces for advancement are acting within the coupling elements in devices according to CA 2694017, DE 202007007760U1, DE 000029506512U1, and DE 202008011841U1, because they connect the anterior region of the maxillary rail and in the posterior region of the mandibular rail. The coupling elements are partly designed as rigid rods, partly elastic, and like a telescope, are partially adjustable length by spindle mechanics.

Such solutions are bulky, and therefore not very comfortable to wear, are not easy to clean, are mechanically relatively complex and are expensive to produce. The mentioned devices with tensile force transmission kinematics lead to increased advancement of the mandibula when opening the mouth. This can lead to a locking situation, i.e. the mouth cannot be opened above a certain aperture. When trying to open the mouth further, resulting withdrawing forces would remove the rails from the dental arches. In this manner, the effect of the system would be lost. Attempts have been proposed to resolve these drawbacks by providing variable-length coupling elements. Nevertheless, it is uncomfortable for the user when the opening of the mouth is prevented or impeded.

A compressive force is transferred through the coupling elements in the devices according to EP1972311A1, EP2081525B1, U.S. Pat. No. 6,012,920, U.S. Pat. No. 6,526,982B1, in which the coupling elements connect in the posterior region of the maxillary rail and in the anterior region of the mandibular rail. With this arrangement, the opening of the mouth is easier and less limited. The kinematic effect during opening causes a reduction of the advancement of the mandible. The buccal arrangement of the coupling elements causes their short length. A coupling element describes a circular arc about the pivot point on the upper jaw rail. Because the circular arc has a small radius even at a relatively small angle, a remarkable loss of advancement is the result. To correct this shortcoming, in EP1972311A1, length adjustment with telescope and spring is proposed. However, since the spring force results in an undesirable mouth opening, a closure device is also necessary. This keeps the mouth shut, but results in loss of the freedom of mandibular movement. The user gets a feeling that the jaw is locked.

Further devices, such as that described in DE 102007050309B3, have two coupling elements, which are fixed only at the posterior ends of the upper and lower jaw rails. They have no joints, but are rigidly connected to the rails. They respond by elastic deformation on opening the mouth. This also leads to a restriction of the mouth opening and causes withdrawing forces on the rails.

A similar solution is proposed in DE102008051221A1. It corresponds to the structure of the above solution, but provides one additional joint for every side in the coupling element. In principle, the kinematics is the same as for models without a joint. Here too, with jaw movement, forces attempt to remove the rails from the dental arch.

All known devices only partially fit to the requirements for the successful spread of mandibular advancement.

Existing deficiencies are: lack of comfort while wearing such rails; lack of free lateral and sagittal movement of the mandible; lack of freedom of tongue space; obstacles to closing the lips; no, or cumbersome, tunability of the advancement by the user; limited longevity because of sensitive precision mechanics; difficult maintenance due to complicated shapes; and high production costs due to expensive, complicated items.

SUMMARY OF THE INVENTION

The above defects are resolved by the present invention. Essential advantages achieved with the invention are based on the fact that it has a coupling element for first and second rails, which is simple, inexpensive to produce and removable without tools. The kinematics of rails and coupling element allows a satisfying movement of the mandible, which is especially important for compliance, also with bruxism and when sneezing or yawning.

BRIEF DESCRIPTION OF THE DRAWINGS

An embodiment of the invention is illustrated in the drawings and will be described in detail below. The drawings are so far simplifications, as the impressions of the teeth are not shown. In the drawings:

FIG. 4.1 shows a side view of a device and a first rail;

FIG. 4.2 shows a section of a first rail;

FIG. 4.3 shows a plan view of the first rail;

FIG. 4.4 an isometric view of the first rail;

FIG. 5.1 shows a plan view of the apparatus with a second rail;

FIG. 5.2 shows a side view of the apparatus with the second rail;

FIG. 5.3 an isometric view of the apparatus with the second rail;

FIG. 6.1 shows an embodiment of the device with a coupling element;

FIG. 6.2 shows a side view of the coupling element;

FIG. 6.3 shows an isometric view of the coupling element;

FIG. 7.1 shows an isometric view of the first rail and the coupling element upon insertion of the first bend;

FIG. 7.2 is a detail of the view of FIG. 7.1;

FIG. 7.3 is an isometric view of the first rail and the coupling element after the insertion of the second bend;

FIG. 7.4 is an isometric view of the first rail and the coupling element in the apex of the coupling element in the lateral through opening;

FIG. 7.5 shows a plan view in a state of complete mounting of the coupling element and the first rail;

FIG. 8.1 shows a side view of first rail and the coupling element at the start of the assembly of the second rail;

FIG. 8.2 is an isometric view of the first rail and coupling element at the start of the second rail mounting;

FIG. 8.3 shows a side view of second rail, first rail and the coupling element in the position for connecting;

FIG. 8.4 an isometric view of second toothed bars, first rail and the coupling element in the position for connecting;

FIG. 8.5 shows a side view of second rail, first rail and the coupling element for mounting in the finished state in which the mouth is open;

FIG. 8.6 is an isometric view of second rail, first rail and mounting the coupling element according to finished state in the open mouth;

FIG. 9.1 shows the coupling with an advanced mandible; and

FIG. 9.2 shows an attempt for further advancement of the mandible.

DETAILED DESCRIPTION OF THE PREFERRED EMBODIMENTS

Figure 1:
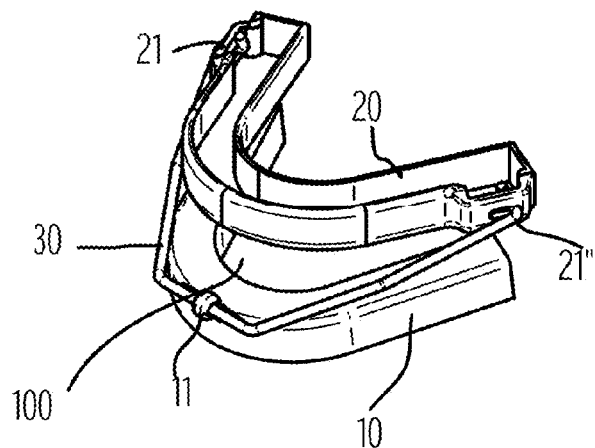
FIG. 1 shows an example of a device as an isometric view with the mouth slightly open.
Figure 2:
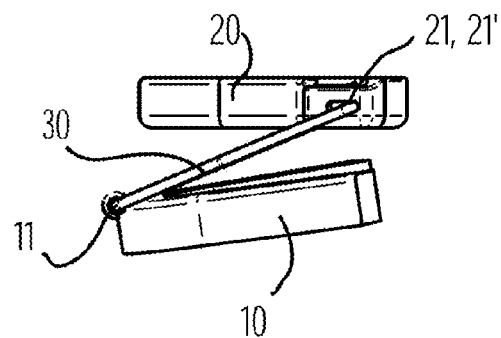
FIG. 2 is an example of a device as a side view with an open mouth.
Figure 3:
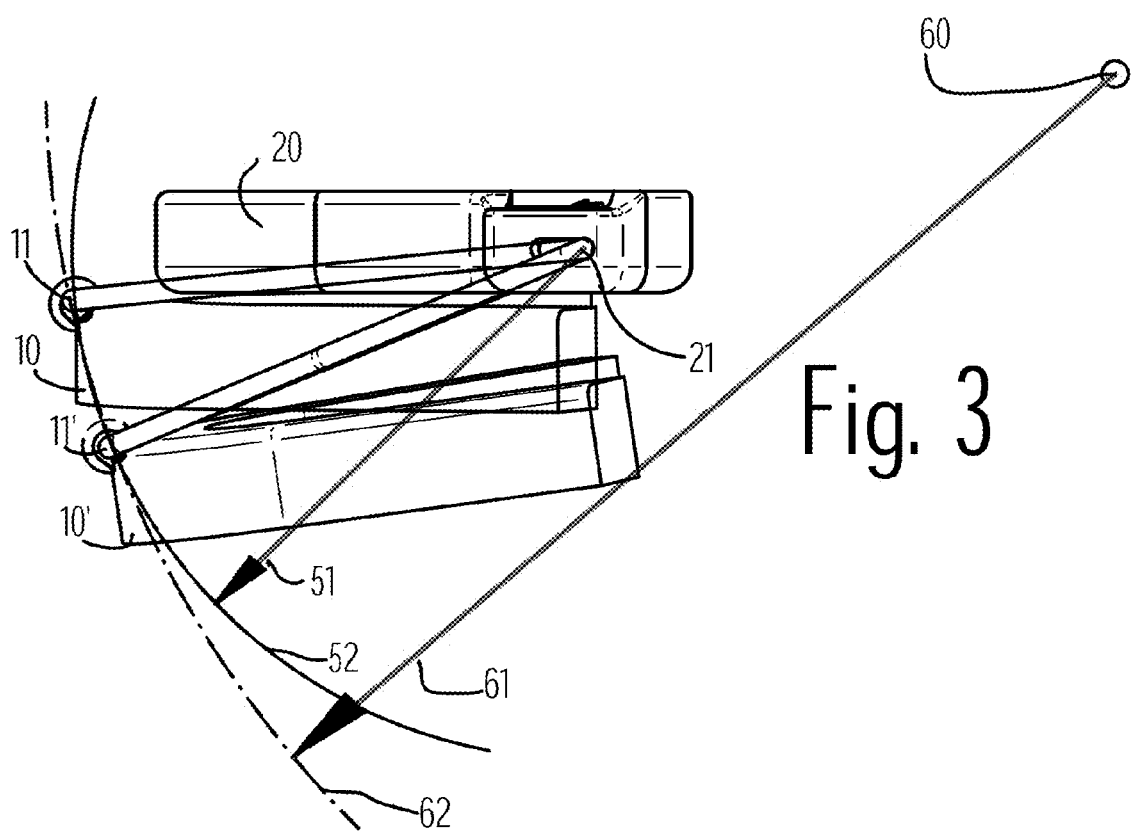
FIG. 3 an example of a device as a side view, with the superposition of the images with the mouth open and mouth closed.

FIGS. 1-3 show a device 100 for improving the breathing of the user with the mouth closed. The device 100 can be used to treat breathing disorders during sleep, such as snoring or sleep apnea, by advancing the lower jaw relative to the upper jaw. This way the airways in the area of the tongue are kept free. During treatment, the device 100 remains within the mouth of the user while the user sleeps.

The apparatus 100 includes the first rail 10 which covers at least some teeth of the lower row of teeth of the user and a second rail 20 which covers at least some teeth of the upper row of teeth of the user. The rails 10 and 20 are preferably provided with impressions of the teeth. Material for the apparatus 100 can be, for example, copolyesters and thermoplastic polyurethane, which are harmless to humans and which allow a comfortable fit.

In the illustrated embodiment, the rails 10 and 20 are connected via a coupling element 30. The first rail 10 has connecting point 11 at the apex of the region of the labial front teeth. The connection point 11 is a bearing for rotation and lateral displacement for the coupling element 30.

The second rail 20 has buccally two rear connection points 21 and 21' in the region of the posterior teeth for the connection of the coupling element 30.

FIG. 2 shows a side view of an example with the mouth slightly open. The coupling element 30, starting from the rear connection points 21 and 21' on the second rail 20, runs on both sides of the dental arches to the front connection point 11 on the first rail 10.

The kinematics of opening the mouth is further illustrated by FIG. 3. When opening the mouth the connecting point 11 of the first rail 10 is moving on an arc 52 around the connection point (21, 21') on the second rail (20) having the radius 51. The radius 51 is dependent only on the dimensions of the coupling element 30. An imaginary arc 62 for constant advancement extends around the center 60 in the jaw joint and having the radius 61. The more similar arcs 52 and 62 are, the more constant is the advancement during opening. In comparison with known devices, the radius 51 of the inventive device is a maximum. This is possible due to the maximum forward position of the connection point 11 on the first rail 10 and the maximum posterior location of the connection points (21, 21') 20 on the second rail. Therefore, the inventive device only slightly decreases the advancement when the mouth is opened. Also the opening of the mouth is in no way restricted by the device.

The first rail in the example shown FIG. 4.1 has the junction 11 in a recess 12 with a lateral opening 13. FIG. 4.1 shows the rail for the lower jaw with the connection point 11 in a recess 12 with a lateral opening 13. The opening 13 communicates with the opening 14, which is an opening of the rail to the inner region of mandibular rail 10 in the direction of the cutting edges of the teeth (incisal). This incisal opening 14 allows the mounting of the two bends, 32, 33 of the angled ends of the coupling element. In the sectional view of FIG. 4.2, which was generated by the one shown in FIG. 4.3 view, the incisal opening 14 and its merger with the lateral opening 13 can be seen. FIG. 4.4 provides a further view of the incisal opening 4.4. The mandibular rail 10 is easily produced and maintained by known methods.

FIGS. 5.1 through 5.3 show an example of the shape of the second rail. Protrusions 22 and 22' can be seen in FIG. 5.1, while FIG. 5.2 shows the protrusions 22, 22' with the slit-shaped openings 23 and 23'. In this example, the slots extend substantially parallel to the occlusal plane. The connection points 21 and 21' are located at the posterior end of the slot-shaped openings 23 and 23'.

The second rail 20 is a very simple component, both in terms of manufacturing as well as for maintenance, as evident from FIG. 5.3

The substantially U-shaped coupling element 30 is shown in FIG. 6.1. This example involves a simple part of bent wire. For ease of manufacturing it is constructed as a symmetrical polygon, which is prepared according to the dimensions of the associated rail. The legs 34 run from apex 31 of the coupling element 30 up to a bend 32, 32'. This bend 32, 32' serves as a bearing shaft in the slot 23, 23' 20 in the second rail 20. Perpendicular to this bend 32, 32' is a further bend 33, 33' (see FIG. 6.2 and FIG. 6.3), which serves to lock the coupling element 30 against disengagement from the second rail 20. For the purpose of user-friendly setting of the advancement, different sized coupling elements are made, which differ in the radius 51 corresponding to the distances between the apex 31 and the bends 32, 32'. By selecting and installing the appropriate size, the desired advancement of the mandible can be set.

With these simple components, the first rail 10, the second rail 20 and the coupling element 30, a functional device is simply assembled by mounting. When mounting is begun, the coupling element 30 is inserted into the first rail 10. As is apparent from FIG. 7.1, the end of the coupling element is inserted into the lateral opening 13, rotated and advanced, and passes with its bends through the opening 13, and eventually after further rotating and advancing enters from the opposite lateral end of the opening 13 (FIG. 7.3). The coupling element 30 then can be continued to be shifted with its leg 34 through the opening 13. This process is shown in FIG. 7.4. When the apex 31 is located in the opening 13 (FIG. 7.5), the mounting of the first rail and the coupling element is finished.

In the drawings, FIG. 8.1 through 8.6, the previously mounted assembly of first rail 10 and coupling element 30 is completed by mounting the second rail 20. In order to do so, the first rail 10 is brought in a position shown in FIGS. 8.1 and 8.2. Then, the second rail 20 is positioned between the bends 33 of the angled ends of the coupling element 30 such that the bends 33 and the slots 23 of the second rail 20 are congruent (FIG. 8.3). Then the bends 33, 33' are guided through the slots 23, until it rests on the inside of the protrusions 22, 22' to emerge (FIG. 8.4). Subsequently the second rail 20 is lowered to the first rail 10. Here, the coupling member 30 rotates relative to the second rail 20. Since the bends 33 and the slots 23 no longer coincide, the coupling element 30 cannot move away from the second rail 20. This is true even if the user has the device in his mouth and opens his mouth because the opening of the mouth is not enough to coincide to the slots 23 and bends 33.

The slots 23 in the second rail 20 have yet another very advantageous function. They allow a check of the set advancement of the mandible. For medical reasons, such a device shall not take full advantage the maximum advancement. With advanced mandible as shown in FIG. 9.1, the coupling element 30 is located with its bend 32, 32' at the posterior end of the slot 23. With proper selection of the size of the coupling member, a reserve for advancement is made available. To test this (FIG. 9.2), the user can attempt to push the lower jaw due to muscle tension to advance even further. If the bend 32, 32' of the coupling element 30 is moved from its position 71 on the posterior end of the slot 23 to the anterior end of the slot 72 such a reserve advancement is available. If this fails, then the coupling element is too large and must be replaced by the next smaller size.

The invention claimed is:

1. An oral device for improving the breathing of a user by means of protrusion of a lower jaw, comprising:
   a first dental rail adapted to cover at least some teeth of a lower row of teeth of the user;
   a second dental rail adapted to cover at least some teeth of an upper row of teeth of the user;
   at least one coupling element connecting the first and the second dental rail;
   wherein the first dental rail comprises a front, labial connection point having a labial protrusion comprising a continuous, laterally directed opening for receiving an apex of the coupling element and forming with it a turning sliding joint, wherein the second dental rail comprises two rear, buccal connection points positioned substantially at its two posterior ends, the buccal connection points each comprising a buccal protrusion with a lateral opening formed as a slit, wherein the coupling element comprises a substantially U-shaped configuration and a posterior, mesial directed first bend on each of its distal ends, wherein the slits and the first bends form a joint on the second dental rail, wherein the apex of the coupling element forms a first joint with the front labial connection point on the first dental rail, and wherein the posterior ends of the coupling element form a second joint with the rear, buccal connection points of the second dental rail.

2. The device according to claim 1, wherein the substantially U-shaped coupling element has a second bend on each end that is substantially perpendicular to the first bend.

3. The device according to claim 2, wherein the buccal connection points have lateral openings formed as slits, wherein a length of one of said openings is at least as great as the length of the second bend of the coupling element.

4. The device according to claim 3, wherein the lateral openings extend substantially parallel to an occlusion plane of the teeth.

5. The device according to claim 1, wherein the size of the coupling element is configured to determine an advancement of a lower jaw of the user, wherein the coupling element is configured to be exchanged without use of tools.

6. The device according to claim 1, wherein the first dental rail, in a region of the laterally directed opening, has an incisal recess that communicates with the laterally directed opening.

7. The device according to claim 1, wherein the substantially U-shaped coupling element is integrally formed from wire.

8. The device according to claim 1, wherein the substantially U-shaped coupling element is formed as a polygon.

9. A method for assembling an oral device for improving the breathing of a user by means of protrusion of a lower jaw, and comprising a first dental rail adapted to cover at least some teeth of a lower row of teeth of the user; a second dental rail adapted to cover at least some teeth of an upper row of teeth of the user; and at least one coupling element connecting the first and the second dental rail, wherein the first dental rail comprises a front, labial connection point and the second dental rail has two rear, buccal connection points positioned substantially at its two posterior ends, wherein the coupling element has a substantially U-shaped configuration, wherein an apex of the coupling element forms a first joint with the front labial connection point on the first dental rail, and wherein the posterior ends of the coupling element form a second joint with the rear, buccal connection points of the second dental rail, comprising the steps of:
   assembling of the coupling element with the first dental rail by inserting an angled end of the coupling element into a laterally directed opening at the front, labial connection point of the first dental rail;
   rotating the coupling element under feed until the angled end passes through a recess in an incisal opening, and further rotating the coupling element under feed so that the angled end exits the laterally directed opening at an opposite side from which it entered at the front labial connection point;
   displacing the coupling element further until a desired functional position in the dental rail is obtained.

10. A method of assembling an oral device for improving the breathing of a user by means of protrusion of a lower jaw, and comprising a first dental rail adapted to cover at least some teeth of a lower row of teeth of the user; a second dental rail adapted to cover at least some teeth of an upper row of teeth of the user; and at least one coupling element connecting the first and the second dental rail, wherein the first dental rail comprises a front, labial connection point and the second dental rail has two rear, buccal connection points positioned substantially at its two posterior ends, wherein the coupling element has a substantially U-shaped configuration, wherein an apex of the coupling element forms a first joint with the front labial connection point on the first dental rail, and wherein the posterior ends of the coupling element form a second joint with the rear, buccal connection points of the second dental rail, comprising the steps of:

- aligning the second dental rail between angled ends of the coupling element;
- aligning slit openings in the buccal connection point with the angled ends of the coupling element;
- passing the angled ends through the slit openings into an interior of the second rail until a pivoting of the second dental rail relative to the coupling element is possible, such that after said pivoting, the angled ends are no longer aligned with the slit openings so that the coupling element is not disconnectable from the second dental rail.

* * * * *